United States Patent
Love et al.

(10) Patent No.: US 6,869,598 B2
(45) Date of Patent: *Mar. 22, 2005

(54) STABILIZATION OF SUNSCREENS IN COSMETIC COMPOSITIONS

(75) Inventors: Arthur Ray Love, Nutley, NJ (US); Judith Lynne Kerschner, Hawthorne, NJ (US); Michael James Barratt, Oak Ridge, NJ (US); Yan Zhou, Montville, NJ (US); Prem Chandar, Closter, NJ (US)

(73) Assignee: Unilever Home & Personal Care USA Division of Conopco, Inc., Greenwich, CT (US)

( * ) Notice: Subject to any disclaimer, the term of this patent is extended or adjusted under 35 U.S.C. 154(b) by 50 days.

This patent is subject to a terminal disclaimer.

(21) Appl. No.: 10/385,914

(22) Filed: Mar. 11, 2003

(65) Prior Publication Data

US 2003/0185773 A1 Oct. 2, 2003

Related U.S. Application Data

(60) Provisional application No. 60/366,908, filed on Mar. 22, 2002.

(51) Int. Cl.$^7$ ............ A61K 7/42; A61K 7/44; A61K 7/00
(52) U.S. Cl. ............ 424/59; 424/60; 424/400; 424/401
(58) Field of Search ............ 424/59, 60, 70.1, 424/400, 401

(56) References Cited

U.S. PATENT DOCUMENTS

| | | |
|---|---|---|
| 4,919,934 A | 4/1990 | Deckner et al. |
| 4,959,393 A | 9/1990 | Torihara et al. |
| 5,188,831 A | 2/1993 | Nicoll et al. |
| 5,219,558 A | 6/1993 | Woodin, Jr. et al. |
| 5,961,961 A | 10/1999 | Dobkowski et al. |

FOREIGN PATENT DOCUMENTS

| | | |
|---|---|---|
| EP | 0 341 664 A1 | 11/1989 |
| EP | 0 904 774 A | 3/1991 |
| GB | 1581428 | 12/1980 |
| JP | 02-292213 | 12/1990 |
| JP | 04-169511 | 6/1992 |
| JP | 04-169516 | 6/1992 |
| JP | 05-004905 | 1/1993 |
| JP | 06 056641 A | 3/1994 |

OTHER PUBLICATIONS

*International Search Report No. PCT/EP 03/02656*, dated Jul. 2, 2003, 3 pp. Database WPI Derwent XP002244752—abstract of JP 06 056641 A.

*Primary Examiner*—Shelley A. Dodson
(74) *Attorney, Agent, or Firm*—Ellen Plotkin

(57) ABSTRACT

Cosmetic compositions containing organic sunscreens along with a 4-substituted resorcinol derivatives of general formula I exhibit improved storage stability and oxidative stability:

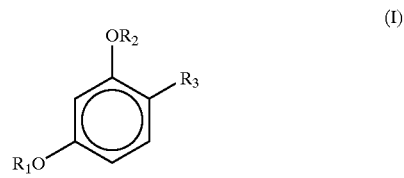

(I)

where each $R_1$ and $R_2$, independently, represents a hydrogen atom, —CO—R (acyl group), —COO—R CONHR; where R represents saturated or unsaturated, linear, branched or cyclic $C_1$–$C_{18}$ hydrocarbon groups; and $R_3$ represents (1) an alkyl group, having from 1 to 18 carbon atoms, preferably having from 2 to 12 carbon atoms, with or without substitution of one or more hydrogen atoms of a linear alkyl group with a methyl or ethyl group; e.g., $R_3$ constitutes linear or branched chain alkyls, or (2) a group of the general formula formula (II)

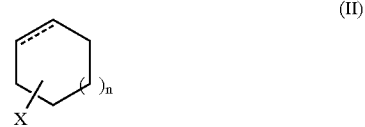

(II)

Where X is preferably H, n is 0 to 3 and the dashed lines represents an optional double bond.

11 Claims, No Drawings

STABILIZATION OF SUNSCREENS IN COSMETIC COMPOSITIONS

This application claims priority under 35 U.S.C. Section 119 from U.S. provisional application Ser. No. 60/366,908 filed Mar. 22, 2002.

FIELD OF THE INVENTION

The invention relates to cosmetic compositions containing organic sunscreens which are stabilized against degradation by incorporation of 4-substituted resorcinol derivatives in the compositions.

BACKGROUND OF THE INVENTION

Certain organic substances, known as sunscreens, whose molecules absorb the harmful ultraviolet rays are widely used in cosmetic compositions to protect human skin against the damaging effects of sunlight. Sunscreens are described in many publications, including Nicoll et al., U.S. Pat. No. 5,188,831 and Dobrowski et al., U.S. Pat. No. 5,961,961. The effectiveness of sunscreens is measured in terms of a property known as the Sun Protection Factor (SPF), as is well know to one skilled in the art.

The ideal sunscreen should be sufficiently chemically and physically stable so as to provide an acceptable shelf life upon storage. It is particularly desirable that the preparation should retain its protective effect over a prolonged period after application. Thus, the active agent when present on the skin must be resistant to chemical or photodegradation, to absorption through the skin, and to removal by perspiration, skin oil, or water.

Sunscreen agents in the order of decreasing effectiveness may be categorized as either highly chromophoric monomeric organic compounds, inorganic compounds and minimally chromophoric polymeric organic solids.

U.S. Pat. No. 5,219,558 (Woodin, Jr. et al.) and U.S. Pat. No. 4,919,934 (Deckner et al.) disclose photoprotection compositions wherein the active sunscreen agents are of the chromophoric monomeric organic compound variety. The examples feature the commercially common sunscreens such as octyl methoxycinnamate (Parsol MCX), benzophenone-3(Oxybenzone) and octyl dimethyl PABA.

Chromophoric monomeric, organic compounds are subject to certain problems. Organic sunscreens, when incorporated in personal care compositions or when deposited on skin, lose their sunscreen properties and may change character with time, due to many factors.

Among many reasons for degradation, one factor responsible for loss of sun screen factor (SPF) or change in character is that organic sunscreens are oxidatively, or photooxidatively, unstable. Instability is an undesirable characteristic in organic sunscreens. There is a need, therefore, for an agent that will stabilize organic sunscreens against degradation. In particular, there is a need for an agent that will prevent the oxidation or photooxidation of organic sunscreens.

SUMMARY OF THE INVENTION

Applicants have now discovered that inclusion of 4-substituted resorcinol derivatives in combination with organic sunscreens in personal care compositions provides oxidative or photooxidative stability to the organic sunscreens. Accordingly, the present invention provides a cosmetic composition comprising:

a. about 0.01 wt. % to about 20 wt. % of an organic sunscreen,
b. about 0.0001 wt. % to about 50 wt. % of a 4-substituted resorcinol derivative of the general formula I

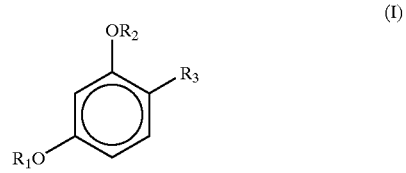

wherein each $R_1$ and $R_2$, independently, represents a hydrogen atom, —CO—R, —COO—R, CONHR; where R represents saturated or unsaturated, linear, branched or cyclic $C_1$–$C_{18}$ hydrocarbon groups; and $R_3$ represents (1) an alkyl group, having from 1 to 18 carbon atoms, preferably having from 2 to 12 carbon atoms, with or without substitution of one or more hydrogen atoms of a linear alkyl group with a methyl or ethyl group; e.g., $R_3$ constitutes linear or branched chain alkyls, or (2) a group of the general formula formula (II)

Wherein X is hydrogen; $OR^1$, wherein $R^1$ represents hydrogen, ($C_1$–$C_6$)alkyl or aryl-($C_1$–$C_6$)alkyl; $OCOR^2$ wherein $R^2$ represents ($C_1$–$C_6$)alkyl, aryl-($C_1$–$C_6$)alkyl or phenyl; halogen; ($C_1$–$C_6$)alkyl; aryl-($C_1$–$C_6$)alkyl, or aryl-($C_1$–$C_6$)alkyl; or $NHR^1$ wherein $R^1$ is defined as above;

wherein n is 0 to 3; and wherein the dashed line indicates an optional double bond; and c. a cosmetically acceptable vehicle.

The inventive compositions are aesthetically pleasing and have improved oxidative or photooxidative stability, which provides longer lasting effect after application to the skin as well as degradation upon storage.

DETAILED DESCRIPTION OF THE INVENTION

As used herein, the term "cosmetic composition" is intended to describe compositions for topical application to human skin, including leave-on and wash-off products.

The term "skin" as used herein includes the skin on the face, neck, chest, back, arms, axillae, hands, legs, and scalp.

The term "inhibit" as it relates to oxidation of sunscreens is intended to describe a decrease in oxidation of sunscreens by at least a certain amount and at most completely.

Except in the examples, or where otherwise explicitly indicated, all numbers in this description indicating amounts of material or conditions of reaction, physical properties of materials and/or use are to be understood as modified by the word "about". All amounts are by weight of the composition, unless otherwise specified.

For the avoidance of doubt the word "comprising" is intended to mean including but not necessarily consisting of or composed of. In other words the listed steps or options need not be exhaustive.

The invention is concerned with a cosmetic composition employing 4-substituted resorcinol derivatives to inhibit the degradation of organic sunscreens present therein. Preferably, in the cosmetic compositions of the present invention, 4-substituted resorcinol derivatives are used to stabilize organic sunscreens against oxidation or photooxidation. Depending upon the nature of the cosmetic composition, other skin benefit materials and/or cosmetic adjuncts can optionally be present, and the 4-substituted resorcinol derivatives may also serve to provide a skin benefit in addition to having a stabilizing function for the sunscreens.

Organic Sunscreens

The inventive cosmetic compositions include an organic sunscreen to provide protection from the harmful effects of excessive exposure to sunlight. Organic sunscreens for purposes of the inventive compositions are organic sunscreen agents having at least one chromophoric group absorbing within the ultraviolet range of from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, .alpha.-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyldibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)] aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Suitable commercially available organic sunscreen agents are those identified under the following table.

TABLE 1

| CTFA Name | Trade Name | Supplier |
| --- | --- | --- |
| Benzophenone-3 | UVINUL M-40 | BASF Chemical Co. |
| Benzophenone-4 | UVINUL MS-40 | BASF Chemical Co. |
| Benzophenone-8 DEA | SPECRA-SORB UV-24 | American Cyanamide |
| Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Hunko Chemical |
| Methyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| Octyl salicylate | SUNAROME WMO | Felton Worldwide |
| PABA | PABA | National Starch |
| 2-Phenylbenzimidazole-5-sulphonic acid | EUSOLEX 232 | EM Industries |
| TEA salicylate | SUNAROME W | Felton Worldwide |
| 3-(4-methylbenzylidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BASF Chemical Co. |

The amount of the organic sunscreens in the personal care composition is generally in the range of about 0.01% to about 20%, preferably in the range of about 0.1% to about 10%.

Preferred organic sunscreens are PARSOL MCX and Parsol 1789, due to their effectiveness and commercial availability.

4-Substituted Resorcinol Derivatives

Resorcinol derivatives are known compounds and can be readily obtained, for example, by a method wherein a saturated carboxylic acid and resorcinol are condensed in the presence of zinc chloride and the resultant condensate is reduced with zinc amalgam/hydrochloric acid (Lille. J. Bitter, L A. Peiner. V, Tr. Nauch-Issled. Inst. slantsev 1969, No. 18, 127), or by a method wherein resorcinol and a corresponding alkyl alcohol are reacted in the presence of an alumina catalyst at a high temperature of from 200 to 400° C. (British Patent No. 1,581,428).

The inventive compositions generally contain about 0.01 to about 20% of organic sunscreens and about 0.000001 to about 50% of 4-substituted resorcinols. The particular advantage of the inventive compositions is that organic sunscreens can be stabilized by 4-substituted resorcinols against oxidation or photooxidation.

4-Substituted Resorcinols

The stability of the inventive compositions is achieved by the use of an antioxidant agent which comprises, as an effective component, a resorcinol derivative of the following formula (I):

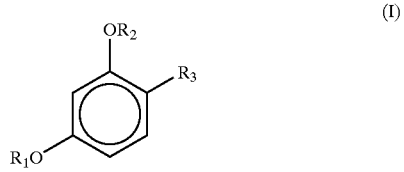

Each $R_1$ and $R_2$, independently, represents a hydrogen atom, —CO—R (acyl group), —COO—R, CONHR groups; where R represents saturated or unsaturated linear, branched or cyclic $C_1$–$C_{18}$ hydrocarbon. In a preferred embodiment, each or both $R_1$ and/or $R_2$ represents hydrogen. In a more preferred embodiment, both $R_1$ and $R_2$ represent hydrogen. $R_3$ represents:

(1) an alkyl group, preferably having from 1 to 18 carbon atoms, preferably 2 to 12 carbon atoms, with or without substitution of one or more hydrogen atoms of a linear alkyl group with a methyl or ethyl group; e.g., $R_3$ constitutes linear or branched chain alkyls, or (2) a group of the general formula formula (II)

Wherein X is hydrogen; $OR^1$, wherein $R^1$ represents hydrogen, $(C_1$–$C_6)$alkyl or aryl-$(C_1$–$C_6)$alkyl; $OCOR^2$ wherein $R^2$ represents $(C_1$–$C_6)$alkyl, aryl-$(C_1$–$C_6)$alkyl or phenyl; halogen; $(C_1$–$C_6)$alkyl; aryl-$(C_1$–$C_6)$alkyl, or aryl-$(C_1$–$C_6)$alkyl; or $NHR^1$ wherein $R^1$ is defined as above;

wherein n is 0 to 3; and wherein the dashed line indicates an optional double bond.

For example, where n is 0, the group of general formula II is a 5-member ring; where n is 1, the group is a 6-member ring; where n is 2, a 7-member ring; and where n is 3, an 8 member ring.

4-Alkyl Substituted Resorcinols

In the above formula (1), the unsubstituted linear alkyl group represented by R and preferably having from 2 to 12 carbon atoms may include an ethyl group, a propyl group, a butyl group, a pentyl group, a hexyl group, a heptyl group, an octyl group, a nonyl group, a decyl group, an undecyl group and a dodecyl group. These linear alkyl groups may be substituted with a methyl or ethyl group at one or more hydrogen atoms thereof. Specific examples of the substituted alkyl group include an isopropyl group, an isobutyl group, an isoamyl group, or a 2-methylhexyl group. Preferred alkyl groups are those where R is an ethyl, propyl, butyl, pentyl, hexyl, heptyl or octyl group. The most preferable alkyl resorcinols are those where R is an ethyl, a butyl or a hexyl group.

4-Cyclo-Substituted Resorcinols

In the above formula (I) where $R^3$ has the general formula II, the compounds are referred to herein as 4-cyclo-substituted resorcinols of general formula III

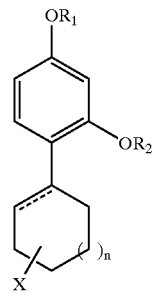

X is hydrogen; $OR^1$, wherein $R^1$ represents hydrogen, $(C_1$–$C_6)$alkyl or aryl-$(C_1$–$C_6)$alkyl; $OCOR^2$ wherein $R^2$ represents $(C_1$–$C_6)$alkyl, aryl-$(C_1$–$C_6)$alkyl or phenyl; halogen; $(C_1$–$C_6)$alkyl; aryl-$(C_1$–$C_6)$alkyl, or aryl-$(C_1$–$C_6)$alkyl; or $NHR^1$ wherein $R^1$ is defined as above;

n is 0 to 3; and the dashed line indicates an optional double bond at that position.

Examples of more specific embodiments of the 4-cyclo-substituted resorcinols include:

(a) compounds of the formula (III) wherein a single bond connects the two carbon atoms at the dashed line;
(b) compounds of the formula (III) wherein n is one;
(c) compounds of the formula (III) wherein X is hydrogen;
(d) compounds of the formula (III) wherein X is hydrogen, methyl or ethyl;
(e) compounds of the formula (III) wherein n is zero;
(f) compounds of the formula (III) wherein n is two; and
(g) compounds of the formula (III) wherein X is benzyloxy.

Preferred compounds of formula (III) are 4-cyclopentylresorcinol, 4-cyclohexyl resorcinol, 4-cycloheptyl resorcinol, and 4-cyclooctyl resorcinol. Most preferred compounds of formula (III) are 4-cyclohexylresorcinol and 4-cyclopentylresorcinol.

An amount of 4-substituted resorcinol derivative effective to inhibit the oxidation of organic sunscreens may be determined by experimentation. The organic sunscreens and 4-substituted resorcinol derivatives are present in the composition in a weight ratio of about 1:1000 to 1000:1, preferably 1:100 to 100:1, more preferably 1:1 to 1:100.

The amount of the resorcinol derivative is preferably in the range of about 0.00001% to about 10%, more preferably about 0.001 to 7%, most preferably from 0.01% to about 5%, of the total amount of a cosmetic composition.

Skin Benefit Agents

Preferred cosmetic compositions are those suitable for the application to human skin, which optionally, but preferably, include a skin benefit agent.

Suitable skin benefit agents include anti-aging, wrinkle-reducing, skin whitening, anti-acne, and sebum reduction agents. Examples of these include alpha-hydroxy acids and esters, beta-hydroxy acids and ester, polyhydroxy acids and esters, kojic acid and esters, ferulic acid and ferulate derivatives, vanillic acid and esters, dioic acids (such as sebacid and azoleic acids) and esters, retinol, retinal, retinyl esters, hydroquinone, t-butyl hydroquinone, mulberry extract, licorice extract, and resorcinol derivatives other than the 4-substituted resorcinol derivatives discussed hereinabove (thereby serving a dual function of providing oxidative stabilization of organic sunscreens and of providing a skin benefit, such as lightening for example).

Cosmetically Acceptable Carrier

The skin benefit agent together with the organic sunscreen compound and resorcinol derivative of the invention is usually used along with a cosmetic base. Suitable cosmetic carriers are well known to one skilled in the art. The cosmetic bases may be any bases which are ordinarily used for skin benefit agents and are not thus critical. Specific preparations of the cosmetics to which the skin benefit agents of the invention is applicable include creams, ointments, emulsions, lotions, oils, packs and nonwoven wipes. Cream bases are, for example, beeswax, cetyl alcohol, stearic acid, glycerine, propylene glycol, propylene glycol monostearate, polyoxyethylene cetyl ether and the like. Lotion bases include, for example, oleyl alcohol, ethanol, propylene glycol, glycerine, lauryl ether, sorbitan monolaurate and the like.

The cosmetically acceptable vehicle may act as a dilutant, dispersant or carrier for the skin benefit ingredients in the composition, so as to facilitate their distribution when the composition is applied to the skin.

The vehicle may be aqueous, anhydrous or an emulsion. Preferably, the compositions are aqueous or an emulsion, especially water-in-oil or oil-in-water emulsion, preferentially oil in water emulsion. Water when present will be in amounts which may range from 5 to 99%, preferably from 20 to 70%, optimally between 40 and 70% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as cosmetically acceptable carriers.

These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterol esters, of which cholesterol fatty acid esters are examples.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces skin dryness and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. For leave-on products, total concentration of the surfactant will range from 0.1 to 40%, preferably from 1 to 20%, optimally from 1 to 5% by weight of the composition. For wash-off products, such as cleansers and soap, total concentration of surfactant will range at about 1 to about 90%. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable non-ionic surfactants.

Preferred anionic surfactants include soap, alkyl ether sulfate and sulfonates, alkyl sulfates and sulfonates, alkylbenzene sulfonates, alkyl and dialkyl sulfosuccinates, $C8–C_{20}$ acyl isethionates, acyl glutamates, $C_8–C_{20}$ alkyl ether phosphates and combinations thereof.

The inventive cosmetic compositions optionally contain a lathering surfactant. By a "lathering surfactant" is meant a surfactant which, when combined with water and mechanically agitated, generates a foam or lather. Preferably, the lathering surfactant should be mild, meaning that it must provide sufficient cleansing or detergent benefits but not overly dry the skin, and yet meet the lathering criteria described above. The cosmetic compositions of the present invention may contain a lathering surfactant in a concentration of about 0.01% to about 50%.

Optional Components

In the cosmetic compositions of the invention, there may be added various other plasticizers, elastomers, calamine, pigments, antioxidants, chelating agents, and perfumes, as well as additional sunscreens such UV diffusing agents, typical of which is finely divided titanium oxide and zinc oxide.

Other adjunct minor components may also be incorporated into the cosmetic compositions. These ingredients may include coloring agents, opacifiers, and perfumes. Amounts of these other adjunct minor components may range anywhere from 0.001% up to 20% by weight of the composition.

Use of the Composition

The composition according to the invention is intended primarily as a personal care product for topical application to human skin, as well as to protect exposed skin from the harmful effects of excessive exposure to sunlight.

In use, a small quantity of the composition, for example about 0.1 to about 5 ml, is applied to exposed areas of the skin, from a suitable container or applicator and, if necessary, it is then spread over and/or rubbed into the skin using the hand or fingers or a suitable device.

Product Form and Packaging

The cosmetic composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto. In all examples, organic sunscreens were obtained from Givaudan Corp.

EXAMPLES 1–8

A set of compositions within the scope of the present invention were prepared and listed in the Table below. The composition is in weight percent.

TABLE 2

| Ingredient Trade and CTFA Name | Phase | 1 | 2 | 3 | 4 | 5 | 6 | 7 | 8 Base |
|---|---|---|---|---|---|---|---|---|---|
| Stearic acid | A | 14.9 | 14.9 | 12.9 | 17.9 | 14.0 | 14.0 | 14.0 | 14.0 |
| Sodium cetearyl sulfate | A | 1.0 | 1.0 | 1.5 | 1.5 | 1 | 1 | 1 | 1 |
| Myrj 59 | A | 2.0 | 1.5 | 2 | 2 | 2 | 2 | 2 | 2 |
| Span 60 | A | 2.0 | 1.5 | 2 | 2 | 2 | 2 | 2 | 2 |
| Propyl paraben | A | 0.10 | 0.10 | 0.10 | 0.10 | 0.10 | 0.10 | 0.10 | 0.10 |
| BHT | A | 0.1 | 0.1 | 0.1 | 0.1 | 0.1 | 0.1 | 0.1 | 0.1 |
| Dimethicone | A |  | 0.50 | 0.75 |  | 0.75 | 0.75 | 0.75 | 0.75 |
| Water | B | BAL* | BAL | BAL | BAL | BAL | BAL | BAL | BAL |
| EDTA | B | 0.04 | 0.04 | 0.04 | 0.04 | 0.04 | 0.04 | 0.04 | 0.04 |
| Pamulen TR 2 | B |  | 0.10 | 0.05 |  | 0.05 | 0.05 | 0.05 | 0.05 |
| Methyl paraben | B | 0.15 | 0.15 | 0.15 | 0.15 | 0.15 | 0.15 | 0.15 | 0.15 |
| Parsol MCX (organic sunscreen) | C | 0.75 | 1.25 | 1 | 1 | 0.75 | 0.75 | 0.75 | 0.75 |
| Parsol 1789 (organic sunscreen) | C | 0.40 |  | 0.4 | 0.4 | 0.4 | 0.4 | 0.4 | 0.4 |
| Micronized Titanium oxide | C |  |  |  |  | 0.2 | 0.2 | 0.2 | 0.2 |
| Propylene glycol | D |  |  |  |  | 8 | 8 | 8 | 8 |
| Transcutol | D |  |  |  |  | 4 | 4 | 4 | 4 |
| 4-butyl resorcinol | D | 0.05 | 2.0 | 2.0 | 3.5 |  |  |  |  |
| 4-ethyl resorcinol | D |  |  |  |  | 2.5 |  |  |  |
| 4-hexyl resorcinol | D |  |  |  |  |  |  | 3.51 |  |
| 4-hexyl resorcinol diacetate | D |  |  |  |  |  |  |  | 5.0 |

*BAL = balanced to 100%

The compositions of Examples 1–7 in the Table above, as well as Example 8 which is the base composition without addition of any resorcinol derivative, were prepared in the following fashion. Phase A is heated at 75° C. Phase B is heated to 75° C. in a container separate from that of Phase A. Thereafter the phases are combined with mixing with heat being turned off. Phase C was premixed and warmed then added immediately after phase A and B mixed. Phase D is pre-dissolved and added into the main pot at 60° C. The mixture is cooled until 40° C. and then packed.

EXAMPLE 9

The photo-stability of organic sunscreens in various cosmetic compositions was measured in the presence and absence of resorcinol derivatives. Examples 5 to 8 in the Table above were tested for this purpose. The resorcinol derivatives in these examples were tested at equivalent molar concentrations in the formulations (18.09 mM). The photo-stability of a UVA organic sunscreen, Parsol 1789, in these compositions was assessed by monitoring the loss of Monochromatic Protection Factor (MPF) over time, as outlined below. A comparative composition (example 8) was made by removing the resorcinol derivative from the compositions in examples 5 to 7.

Procedure for Measuring MPF of Cosmetic Formulations

An SPF-290 Analyzer with an integrating sphere from Optometrics USA was used to acquire the MPF data. The software generates a Monochromatic Protection Factor (MPF) for each 5 nm portion of the scan from 290 nm to 400 nm. The MPF is calculated from the reciprocal of the transmission (MPF=$1/T_\lambda$) at each of these wavelengths ($\lambda$ or gamma). MPF is an indication of the UV protective properties of a skin composition, since the SPF, or sun protection factor, is a weighted average of MPF values at different wavelengths across the UV spectrum. A drop in MPF over time, therefore, indicates loss of sunscreen activity.

The SPF-290 instrument light source is a 125 W xenon arc lamp, operated at 75W, whose beam passes through a wire attenuator and a Schott UG05 filter. The filter attenuates the source radiation above 500 nm and alters the spectral distribution to approximate the relative solar irradiance spectrum in the UV-B and UV-A regions. The intensity of the beam incident on the sample is approximately 6 mW/cm$^2$, corresponding to approximately 8 times the solar UV intensity at midday in summer in the Northeast US. The minimum time of test site exposure to the UV beam required for each complete scan is approximately 30 seconds. After passing through the sample, the radiation is collected in the integrating sphere and separated into discrete wavelength bands with an in-line Fastie-Ebert grating monochromator optimized for UV efficiency. The bands strike the detector and generate a signal proportional to intensity of the radiation. The MPF value at 360 nm (UVA) was used for sunscreen photo-stability evaluation in the examples 5–8.

A UV-Transparent quartz plate (4"×4⅛×⅛") was first calibrated by placing it on the automated programmable X-Y stage and scanned to correct for background. The product film was then applied evenly to the calibrated quartz plate with a spatula. An 8-path wet film applicator (Paul Gardner Company, Inc.) was used with a 3" path width. The applicator was manually drawn across the plate using the 1.5 mils gap (1 mil=0.001 inches or approximately 25 micro-meters) and the film allowed to dry for 15 minutes. The quartz plate with the product film was then placed on the X-Y stage and scanned for the baseline measurement (t=0). The X-Y stage was set to scan six pre-set sites of the product film. The same six pre-set sites were scanned every 15 minutes up to 105 minutes, while the product formulations were stored in glass amber jars of 120 ml volume at 25° C., to monitor loss of sunscreen performance over time. Between each measurement, the product film was removed from the UV light source and placed in a drawer at ambient temperatures. The MPF values presented in the table represent the average of readings from the six different sites at each time point.

TABLE 3

| | % MPF change from t = 0 | | | |
| --- | --- | --- | --- | --- |
| Time, min. | Comparative, no antioxidant Example 8 | Example 5 (with 4-ethyl resorcinol) | Example 6 (with 4-hexyl resorcinol) | Example 7 (with 4-hexyl resorcinol diacetate) |
| 0 | 0 | 0 | 0 | 0 |
| 15 | −21.8 | −3.6 | −1.0 | 0.2 |
| 30 | −23.8 | −8.3 | −1.7 | 1.6 |
| 45 | −32.0 | −10.1 | −0.4 | 3.4 |
| 60 | −39.0 | −11.2 | −1.5 | 2.7 |
| 75 | −44.2 | −14.6 | −2.1 | 4.5 |
| 90 | −48.6 | −17.4 | −3.8 | −1.4 |
| 105 | −51.8 | −20.9 | −8.3 | −2.3 |
| p-value* | <0.0001 | <0.0001 | <0.0001 | <0.0001 |

*p-values of less than 0.05 indicate statistical significance, i.e., a Significant difference between no metal oxides (Example 8) and with metal oxides (Examples 5, 6, 7)

The results in the table above demonstrate that addition of resorcinol and derivatives to the compositions of this invention provided additional stability.

The data in the Table above was found to be statistically significant, with p-values of less than 0.0001. The p-values were determined as follows.

Objective—Compare light blockage of the base composition of Example 8 against compositions of Examples 5–7 containing resorcinol derivatives. The products with resorcinol additives are expected to show a slower decrease in light blockage. The inverse of light transmission is used as a virtual measure of light blockage.

Method—The products are applied to glass slides and six spots are measured on each slide. There are three slides for each of the four products. This provides a total of 18 spots for each product. As is standard with studies in sunscreens, 15 minutes elapse for drying until the first measure. Measurements are then taken every 15 minutes until 120 minutes for a total of eight time points. A mixed effects analysis of variance will take into account the spots within slides and the correlation between time points. The analysis of variance looks for effects of time, product and time with product interactions. A significant time with product interaction will show if there is any difference in the rate of change in light blockage among the products. A contrast comparison will determine if the rate of change for the Example 8 base is significantly different from the three products with resorcinol. Regression models for each product will fit a function to the data for each product. The functions will assess the relationship between time with inverse light transmission. The functions will assess the linear effect of time.

Results—There are overall significant product, time, product with time interactions effects with p-values less than 0.0001. The contrast shows a significant difference of p=0.0001 between the composition of Example 8 and the resorcinol derivative containing compositions of Examples 5–7.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A personal care composition comprising:
    a. about 0.01 wt. % to about 20 wt. % of an organic sunscreen,
    b. about 0.0001 wt. % to about 50 wt. % of a 4-substituted resorcinol derivative of general formula I

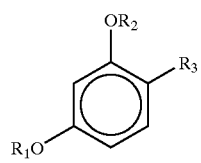

(I)

wherein each $R_1$ and $R_2$, independently, represents a hydrogen atom, —CO—R, —COO—R, CONHR; where R represents saturated or unsaturated, linear, branched or cyclic $C_1$–$C_{18}$ hydrocarbon groups; and $R_3$ represents an alkyl group having from 1 to 18 carbon atoms or a group of the general formula formula (II)

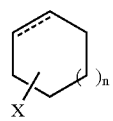

(II)

Wherein X is hydrogen; $OR^1$, wherein $R^1$ represents hydrogen, ($C_1$–$C_6$)alkyl or aryl-($C_1$–$C_6$)alkyl; $OCOR^2$ wherein $R^2$ represents ($C_1$–$C_6$)alkyl, aryl-($C_1$–$C_6$)alkyl or phenyl; halogen; ($C_1$–$C_6$)alkyl; aryl-($C_1$–$C_6$)alkyl, or aryl-($C_1$–$C_6$)alkyl; or $NHR^1$ wherein $R^1$ is defined as above;

n is 0 to 3; and wherein the dashed line indicates an optional double bond; and c. a cosmetically acceptable carrier.

2. The composition of claim 1, wherein said organic sunscreen is selected from the group consisting of Benzophenone-3, Benzophenone-4, Benzophenone-8, DEA, Methoxycinnamate, Ethyl dihydroxypropyl-PABA, Glyceryl PABA, Homosalate, Methyl anthranilate, Octocrylene, Octyl dimethyl PABA, Octyl methoxycinnamate (PARSOL MCX), Octyl salicylate, PABA, 2-Phenylbenzimidazole-5-sulphonic acid, TEA salicylate, 3-(4-methylbenzylidene)-camphor, Benzophenone-1, Benzophenone-2, Benzophenone-6, Benzophenone-12, 4-Isopropyl dibenzoyl methane, Butyl methoxy dibenzoyl methane (PARSOL 1789), Etocrylene, and mixtures thereof.

3. The composition of claim 1, wherein said 4-substituted resorcinol derivative is present in at least an effective amount to inhibit oxidation of said organic sunscreens.

4. The composition of claim 1, wherein said 4-substituted resorcinol derivative is present in an amount of about 0.1 wt. % to about 5 wt. %.

5. The composition of claim 1, wherein the 4-substituted resorcinol is selected from the group consisting of 4-linear alkyl resorciols, 4-branched alkyl resorcinols, 4-cycloalkyl resorcinols, and mixtures thereof.

6. The cosmetic composition of claim 1, wherein the 4-substituted resorcinol is selected from the group consisting of 4-methyl resorcinol, 4-ethyl resorcinol, 4-propyl resorcinol, 4-isopropyl resorcinol, 4-butyl resorcinol, 4-pentyl resorcinol, 4-hexyl resorcinol, 4-heptyl resorcinol, 4-octyl resorcinol, 4-nonyl resorcinol, 4-decyl resorcinol, and mixtures thereof.

7. The cosmetic composition of claim 1, wherein the 4-substituted resorcinol is selected from the group consisting of 4-cyclopentyl resorcinol, 4-cyclohexyl resorcinol, 4-cycloheptyl resorcinol, 4-cyclooctyl resorcinol, and mixtures thereof.

8. The cosmetic composition of claim 1, further comprising a skin benefit agent selected from the group consisting of alpha-hydroxy acids and esters, beta-hydroxy acids and ester, polyhydroxy acids and esters, kojic acid and esters, ferulic acid and ferulate derivatives, vanillic acid and esters, dioic acids and esters, retinol, retinal, retinyl esters, hydroquinone, t-butyl hydroquinone, mulberry extract, licorice extract, resorcinol derivatives, and mixtures thereof.

9. The cosmetic composition according to claim 6, wherein said 4-substituted resorcinol derivative is present as a skin lightening benefit agent.

10. A cosmetic composition comprising
a. an organic sunscreen stabilized by a 4-substituted resorcinol derivative,
b. a skin benefit agent; and
c. a cosmetically acceptable vehicle
wherein said organic sunscreen is present in an amount of about 1 wt % to about 10 wt % of said cosmetic composition; and
wherein the weight ratio of said organic sunscreen to said 4-substituted resorcinol derivative is about 10000:1 to about 1:10000.

11. The cosmetic composition according to claim 9, wherein said skin benefit agent is selected from the group consisting of alpha-hydroxy acids, beta-hydroxy acids, polyhydroxy acids, hydroquinone, t-butyl hydroquinone, 4-substituted resorcinol derivatives, and mixtures thereof.

* * * * *